United States Patent [19]

Prieels et al.

[11] Patent Number: 4,957,749

[45] Date of Patent: Sep. 18, 1990

[54] PROCESS FOR REMOVING OXYGEN IN FOODSTUFFS AND DRINKS

[75] Inventors: Jean-Paul Prieels; Charles Maschelein; Marc Heilporn, all of Brussels, Belgium

[73] Assignee: Oleofina, S.A., Brussels, Belgium

[21] Appl. No.: 863,269

[22] Filed: May 14, 1986

[30] Foreign Application Priority Data

May 22, 1985 [LU] Luxembourg ............................ 85910

[51] Int. Cl.$^5$ ................................................ A23L 3/00
[52] U.S. Cl. ........................................... 426/10; 426/4;
426/61; 426/321; 426/330; 426/330.2;
426/330.4; 426/330.5; 426/334; 426/7;
426/541; 426/592; 426/16; 426/12
[58] Field of Search ................... 426/61, 4, 10, 11–12,
426/49, 16, 5, 52, 61, 599, 321–330,
330.2–330.5, 334, 333, 541, 590, 592, 594–596,
580, 588, 8; 435/189

[56] References Cited

U.S. PATENT DOCUMENTS

| | | | |
|---|---|---|---|
| 2,482,724 | 9/1949 | Baker | 426/10 |
| 2,891,868 | 6/1959 | Heggie et al. | 426/10 |
| 2,940,860 | 6/1960 | Sarett | 426/10 |
| 3,920,521 | 11/1975 | Michelson et al. | 426/61 |
| 4,029,819 | 6/1977 | Michelson | 426/61 |
| 4,479,971 | 10/1984 | Eng et al. | 426/590 |

FOREIGN PATENT DOCUMENTS 2520792  11/1976  Fed. Rep. of Germany ........ 426/10

OTHER PUBLICATIONS

Jay, "Modern Food Microbiology", Publ. by D. Van Nostrand Company, 1978; p. 31.

*Primary Examiner*—Marianne Cintins
*Attorney, Agent, or Firm*—Michael J. Caddell; John K. Abokhair; M. Norwood Cheairs

[57] ABSTRACT

The present invention relates to a process for removing both molecular and free-radical oxygen from foodstuff materials capable of being degraded by oxidation. The invention is accomplished by the incorporation into foodstuff materials of an enzyme composition containing an oxidase and its substrate, catalase and superoxide dismutase.

14 Claims, No Drawings

PROCESS FOR REMOVING OXYGEN IN FOODSTUFFS AND DRINKS

FIELD OF THE INVENTION

The present invention relates to a process for removing oxygen present in foodstuffs or drinks. In particular, the present invention relates to a process for removing both molecular oxygen and free-radical oxygen present in drinks and more especially in drinks having an acid pH, such as beer. The present invention also relates to an enzyme composition containing superoxide dismutase, which composition is used for carrying out the process of the invention.

BACKGROUND OF THE INVENTION

In the field of the preservation of foodstuffs and drinks in particular, the deleterious effects of oxygen present in aqueous solution are well known. In this instance, these effects result in changes in color and changes in taste. These effects are due mainly to the free radicals formed during the reaction of oxygen with reducing solutes. In order to reduce these deleterious effects of oxygen, antioxidant agents are used.

Various systems which are used for removing oxygen from foodstuffs or drinks are known, such as, for example, catalase and oxidoreductases which are used for protecting foodstuffs against degradation effects due to oxygen. This system significantly reduces the concentration of dissolved oxygen, but it unfortunately has no effect on oxygen present in free-radical form. Free-radical oxygen is responsible for degradation mechanisms.

Systems which employ superoxide dismutase alone are known. In particular, reference is made to U.S. Pat. No. 3,920,521, which is hereby incorporated by reference in its entirety. However, superoxide dismutase does not actually consume oxygen, and it does not prevent all reactions with the different reducing agents in the medium. According to reaction (1), superoxide dismutase traps the superoxide ion and reforms oxygen.

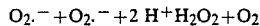
$$O_2.^- + O_2.^- + 2 H^+ \rightarrow H_2O_2 + O_2$$

Moreover, it is well known that superoxide dismutase has only a weak antioxidant power at a pH below 5, and this is due to the transitory existence of the $O_2.^-$ radical at acid pH, as shown in equations (2) and (3).

$$O_2.^- + H^+ \rightarrow HO_2. \quad (pk = 4.88)$$

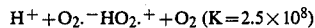
$$H^+ + O_2.^- \rightarrow HO_2.^+ + O_2 \quad (K = 2.5 \times 10^8)$$

At the present time, for the preservation of foodstuffs and especially drinks, either the molecular oxygen is quenched, or an antioxidant is added which will have the effect of maintaining the oxygen content at a certain prescribed content.

In fact, to achieve a considerable improvement in the preservation factor, it appears to be necessary to trap both molecular oxygen and free-radical oxygen, so as to avoid all risk of oxidative degradation of the medium.

SUMMARY OF THE INVENTION

An object of the present invention is to overcome the disadvantages mentioned above.

Another object of the present invention is a process which allows the elimination of both molecular oxygen and free-radical oxygen from foodstuffs and drinks, and especially from drinks the pH of which is below 5.

Yet another object of the present invention is an antioxidant composition containing superoxide dismutase which can be used in the process of the invention.

The process of the present invention, for removing both molecular and free-radical oxygen from foodstuff materials capable of being degraded by oxidation comprises the incorporation therein of an enzyme composition comprising an oxidase and its substrate, catalase and superoxide dismutase.

DETAILED DESCRIPTION OF THE PREFERRED EMBODIMENTS

Applicants have unexpectedly found that, by adding to foodstuff materials, and especially to drinks the pH of which is acidic, an enzyme composition comprising both an oxidase and its substrate, catalase and also superoxide dismutase, a preservation period for these substances is obtained which is distinctly improved, as indicated by considerably reduced oxygen content.

This is all the more unexpected, since it is well known that the antioxidant effect of superoxide dismutase is only very transitory at low pH, for example, as shown by the rate constant of reaction (3) mentioned above.

The foodstuff materials which can be treated include mayonnaise, toothpastes, chewing gums, powdered milk, soluble coffees, and the like.

The process of the invention is especially suitable for treating drinks such as beer, the pH of which is in the region of 4, fruit or vegetable juices, and the like.

The enzyme composition used in the process of the invention necessarily comprises an oxidase and its substrate, except where the latter is already present in the medium, catalase and superoxide dismutase. The joint use of these three enzymes may be regarded as giving rise to a synergistic effect from the standpoint of the antioxidant properties. In effect, when these enzymes are used alone or even mixed in pairs, the results are far from conclusive, and offer no incentive to those versed in the art to combine them.

The enzyme composition used in the process of the invention comprises, first, an oxidase and its substrate. Suitable oxidases include glucose oxidase, oxalate oxidase, lactate oxidase and amino-acid oxidases; the substrates to be used are obviously glucose, oxalic acid, lactic acid and the corresponding amino acids.

All these oxidases are commercially available. It is nevertheless preferable to use glucose oxidase due to availability, cost, and other convenience factors.

The amount of oxidase employed is generally from about 0.1 to about 1 ppm based on the medium. When ppm is utilized herein, a weight/volume unit, i.e., micrograms per liter, is intended. In the case where glucose oxidase is used, its content can be expressed in Sorret units, and this is generally between 25 and 100 Sorret units/l of medium. The Sorret unit is the amount of enzyme which consumes 10 ml. $O_2$ per minute at pH 5.6, in the presence of 3% glucose and oxygen-saturated air, at 30° C. and in the presence of excess catalase.

The substrate is introduced into the medium, except if it is already present in sufficient amounts therein, in the proportion of 0.05 to 2% (wt./vol, i.e., g/100 c.c.), and preferably 0.1 to 1%, based on the medium.

The second enzyme used in the composition of the invention consists of catalase. Catalase is also an enzyme which is well known for its antioxidant action when used with an oxidase. However, catalase alone or mixed with superoxide dismutase has virtually no antioxidant effect.

According to the process of the invention, catalase is used in the proportion of from about 2,000 to about 20,000 units per liter of medium, and preferably from about 5,000 to about 12,000 units/liter of medium. The units of catalase are micromoles of product formed ($O_2$) per minute per mg of enzyme. Catalase is commercially available and, in some cases is present with the oxidase, for example, with glucose oxidase.

The enzyme composition of the invention also comprises superoxide dismutase.

Superoxide dismutase is introduced into the medium in the proportion of from about 0.3 to about 1.5 ppm, and preferably from 0.5 to 1 ppm. The superoxide dismutase used in the composition of the invention can originate from any suitable source, such as erythrocytes or alternatively marine bacterial strains such as *Photobacterium Phosphoreum*, *Phosphoreum leiognathi* and *Phosphobacterium Sepia*.

Applicants unexpectedly found that the joint use of these three enzymes made it possible to achieve an elimination of both molecular and free-radical oxygen which was far superior to that obtained with the usual systems. Moreover, the process and the composition of the present invention are especially applicable to drinks having a low pH, in particular below 5, such as beer.

It has, indeed, been noted that, with the composition of the invention, the concentration of oxygen dissolved in beer is reduced to only a few tens of ppb whereas, with the usual antioxidant systems such as ascorbic acid, residual oxygen remains at a level of between 200 and 500 ppb.

EXAMPLE 1

An enzyme composition comprising glucose oxidase, glucose as substrate, catalase and superoxide dismutase is introduced into a 25-cl bottle of beer of pH 4.2.

Glucose oxidase (GOD) was used in the proportion of 0.5 ppm/1 of medium. Glucose was then added in the proportion of 0.1% based on the medium. Superoxide dismutase (SOD) was added in the proportion of 1 ppm per liter.

After the enzyme composition was introduced into the beer, the bottle was sealed and the resistance of the medium to aging was studied by bringing the beer to a temperature of 50° C. for 40 hours.

The resistance to aging was measured by the thiobarbituric acid test. This test enables the amount of carbonyl products formed by oxidation of the beer to be determined by a colorimetric method. After the beer is cooled, a 5-ml sample is taken therefrom and introduced into a 15-ml tube containing 2 ml of a solution containing 0.33% of thiobarbituric acid in an acetic acid/water (50:50) mixture. After the contents are mixed, the tube is brought to 60° C. for 1 hour and cooled, and the absorbance is read at 530 nm. The absorbance is stated as a % of the highest value, taken as equal to 100%, a high value signifying improved resistance.

With the composition of the invention, a value of 100% was obtained.

By way of comparison, the resistance of a beer to which only GOD, glucose, and catalase were added, in the same proportions as hereabove was determined. As control sample, a beer which had been aerated was also tested.

The results were as follows:
control 37.11%
GOD+glucose+catalase: 84.25%.

This shows that, by applying the process of the invention, a beer is obtained which has a much longer life.

EXAMPLE 2

An enzyme composition comprising glucose oxidase in the proportion of 0.5 ppm/1 of medium, glucose in the proportion of 0.1% based on the medium and 0.5 ppm/1 of SOD was introduced into a 25-cl bottle of beer of pH 4.2.

After this composition was introduced into the beer, the bottle was sealed and the reducing power of the beer was studied by bringing the beer to a temperature of 50° C. for 40 hours.

The reducing power of the beer was determined by measuring the reduction of the (colorless) dipyridyl/$Fe^{3+}$ complex to (red) dipyridyl/$Fe^{2+}$ by means of the reducing substances in the beer.

The absorbance is measured at 510 nm.

The absorbance value of the cool, non-aerated beer is taken as equal to 100%.

With the composition of the invention, an absorbance of 93.3% was obtained.

By way of comparison, the reducing power was determined of a beer to which only GOD, glucose and catalase were added in the same proportions as above.

As a control, an aerated sample was also taken.

The results were as follows:
control: 85.9%
GOD+glucose+catalase: 88.6%

This shows that the beer treated with the composition of the invention has improved reducing power.

EXAMPLE 3

Different enzyme systems and other systems based on ascorbic acid were tested for removal of oxygen from beer, the oxygen being responsible for the loss in flavor and other degradation reactions.

Various compositions, listed in Table I, were hence added to different 25-cl bottles of beer, the pH of the beer being 4.2.

After 10 ml of air were injected per bottle, the antioxidant composition was added, and the bottle was resealed and agitated at 100 rpm at a temperature of 25° C. for 64 hours.

The content of dissolved oxygen in the beer was determined. All the results are shown in Table I.

TABLE I

| Experiment | Composition | Content of Dissolved $O_2$ (ppm) |
|---|---|---|
| 1 | Control - aerated | 3.19 |
| 2 | GOD (50 Sorett units/l) + catalase ($10^4$ U.) + glucose (0.25%) | 0.05 |
| 3 | Catalase ($10^4$ U) | 3.73 |
| 4 | SOD (0.5 ppm) | 3.55 |
| 5 | SOD (0.5 ppm) + catalase ($10^4$ U) | 3.61 |
| 6 | GOD (50 sorett units) + catalase ($10^4$ U) + 0.5% glucose + SOD 0.5 ppm | 0.00 |
| 7 | Ascorbic acid (30 ppm) | 2.86 |

This example shows that only the composition of the invention shows complete removal of the dissolved oxygen.

What is claimed is:

1. A process for preventing the oxidation of foodstuff materials capable of being degraded by oxidation with molecular oxygen, free radical oxygen, or combinations thereof comprising incorporating into said foodstuff materials an amount of an enzyme composition sufficient to reduce the oxygen content of said foodstuff materials, wherein said enzyme composition comprises an oxidase and its corresponding substrate, catalase and superoxide dismutase.

2. The process of claim 1, wherein the foodstuff materials are members of the group consisting of mayonnaise, chewing gums, powdered milk, soluble coffees, beer, fruit juices and vegetable juices.

3. The process of claim 1, wherein the oxidase is selected from the group consisting of glucose oxidase, oxalate oxidase, lactate oxidase and amino-acid oxidases, and the corresponding substrate is selected from the group consisting of glucose, oxalic acid, lactic acid and the corresponding amino acids.

4. The process of claim 1, wherein (a) the oxidase is present in an amount of from about 0.1 to about 1 ppm liter of foodstuff material, (b) the substrate is present in an amount from about 0.05 to about 2% based on the foodstuff material, (c) the catalase is present in an amount from about 2,000 to about 20,000 units per liter of the foodstuff material, and (d) the superoxide dismutase is present in an amount from about 0.3 to about 1.5 ppm per liter of the foodstuff material.

5. The process of claim 4, wherein the catalase is in an amount of from about 5,000 to 12,000 units and the superoxide dismutase is present in an amount of from about 0.5 to about 1 ppm per liter of foodstuff material.

6. The process according to claim 1 wherein the foodstuff material is selected from drinks having a pH below about 5.

7. A process for preventing the autoxidation of beer comprising incorporating into the beer an enzyme composition comprising:
(a) from about 0.1 to about 1 ppm per liter of beer of glucose oxidase,
(b) from about 0.5 to about 2% of glucose,
(c) from about 2,000 to about 20,000 units of catalase per liter of beer, and
(d) from about 0.3 to about 1.5 ppm per liter of beer of superoxide dismutase.

8. A process for preventing the autoxidation of foodstuff materials comprising incorporating into said foodstuff materials amounts of an enzyme composition sufficient to improve the preservation period of said foodstuff materials, wherein said enzyme composition comprises an oxidase, about 2,000 to 20,000 units of catalase per liter of foodstuff material, and about 0.3 to 1.5 ppm of dismutase per liter of foodstuff material, wherein a substrate corresponding to the oxidase is present in said foodstuff material.

9. The process according to claim 8 wherein the oxidase is selected from the group consisting of glucose oxidase, oxalate oxidase, lactate oxidase and amino-acid oxidases, and the corresponding substrate is present in the foodstuff material for to the addition of the enzyme composition and is selected from the group consisting of glucose, oxalic acid, lactic acid and the corresponding amino acids.

10. The process according to claim 8 wherein the oxidase is glucose oxidase present in a concentration of about 0.1 to 1 ppm per liter of foodstuff material and the substrate is glucose added with the enzyme composition in a concentration of about 0.5 to 2% based on the foodstuff material.

11. A process for preventing the autoxidation of foodstuff materials capable of being degraded by oxidation by molecular oxygen, free-radical oxygen or combinations thereof comprising incorporating into said foodstuff materials in amount of an enzyme composition sufficient to reduce the oxygen content of said foodstuff materials, wherein said enzyme composition consists essentially of an oxidase and its corresponding substrate, catalase and superoxide dismutase.

12. The process of claim 11, wherein the foodstuff materials are members of the group consisting of mayonnaise, chewing gums, powdered milk, soluble coffees, beer, fruit juices and vegetable juices.

13. The process of claim 11, wherein the oxidase is selected from the group consisting of glucose oxidase, oxalate oxidase, lactate oxidase and amino-acid oxidases, and the corresponding substrate is selected from the group consisting of glucose, oxalic acid, lactic acid and corresponding amino acids.

14. The process of claim 11, wherein (a) the oxidase is present in an amount from about 0.1 to 1 ppm per liter of foodstuff materials, (b) the substrate is present in an amount from about 0 to 2% based on the foodstuff materials, (c) the catalase is present in amount from about 2,000 to 20,000 units per liter of foodstuff materials, and (d) the superoxide dismutase is present in an amount from about 0.3 to 1.5 ppm per liter of foodstuff materials.

* * * * *